United States Patent [19]

Voorhees

[11] 4,007,268
[45] Feb. 8, 1977

[54] PROCESS FOR ALLEVIATING PROLIFERATIVE SKIN DISEASES

[75] Inventor: John J. Voorhees, Ann Arbor, Mich.

[73] Assignee: The Regents of the University of Michigan, Ann Arbor, Mich.

[22] Filed: May 22, 1975

[21] Appl. No.: 580,014

Related U.S. Application Data

[63] Continuation-in-part of Ser. Nos. 324,012, Jan. 16, 1973, abandoned, and Ser. No. 425,063, Dec. 17, 1963, abandoned.

[52] U.S. Cl. .............................................. 424/200
[51] Int. Cl.$^2$ .................................... A61K 31/675
[58] Field of Search ................................... 424/200

[56] References Cited

FOREIGN PATENTS OR APPLICATIONS 1,440,795   4/1966   France

OTHER PUBLICATIONS

Smith et al. – Chem. Abst., vol. 67 (1967), p. 78,977b.
Karasek et al. – Chem. Abst., vol. 79 (1973), p. 61356y (Abst. of 1971 pub.).
Izutsu et al. – Chem. Abst., vol. 65 (1966), p. 2845f.
Voorhees et al. – Adv. in Cyclic Nucleotide Research, vol. 5 (1975).

*Primary Examiner*—Sam Rosen
*Attorney, Agent, or Firm*—Neal A. Waldrop

[57] ABSTRACT

A process and pharmaceutical composition for alleviating proliferative skin diseases such as psoriasis, atopic dermatitis, etc., comprising administering to humans, or domesticated animals, topically, and/or parenterally, and/or systemically a composition comprising a pharmaceutical carrier and at least one active compound selected from c-AMP analogs and antiviral agents.

4 Claims, No Drawings

PROCESS FOR ALLEVIATING PROLIFERATIVE SKIN DISEASES

CROSS-REFERENCE TO RELATED APPLICATIONS

This application is a continuation-in-part of prior application Ser. No. 324,012, filed Jan. 16, 1973, for "Pharmaceutical Composition and Process of Treatment", now abandoned and prior copending application Ser. No. 425,063, filed Dec. 17, 1963, entitled "Pharmaceutical Composition and Process for Alleviating Proliferative Skin Diseases", now abandoned.

BRIEF DESCRIPTION OF THE INVENTION

This invention relates to pharmaceutical compositions for application to the skin and to a method for the treatment of proliferating skin diseases. The compositions may be applied topically, or by injection such that the composition enters the blood stream or intralesionally, intradermally, or sub-cutaneously or orally. The treatment can be either therapeutic or prophylactic.

DETAILED DESCRIPTION OF THE INVENTION

Proliferative skin diseases are widespread throughout the world and afflict millions of humans and their domesticated animals. This invention provides a method for treatment of such diseases and pharmaceutical compositions which are useful in alleviating them. As used hereinafter in this specification and in the claims, the expression "proliferative skin diseases" means benign proliferative skin diseases which are characterized by epidermal cell proliferation, or division, and may also be associated with incomplete tissue differentiation. Psoriasis is the most serious of the skin diseases with which this invention is concerned. Such diseases include: psoriasis, atopic dermatitis, non-specific dermatitis, primary irritant contact dermatitis, allergic contact dermatitis, lamellar ichthyosis, epidermolytic hyperkeratosis, premalignant sun induced keratosis, non-malignant keratosis, and seborrheic dermatitis in humans and atopic dermatitis and mange in domesticated animals.

Heretofore, proliferative skin diseases have been generally accepted by mankind as an ongoing evil having degrees of severity variable with time, with inherited skin traits and external factors but always have been recognized as unsightly, painful, morbid diseases. Over the history of mankind innumerable medicines and treatments have been proposed, tried and used with varying degrees of success. However, no treatment heretofore devised or pharmaceutical composition used has been entirely successful in the wide spectrum of specific diseases encompassed by the expression proliferative skin diseases.

The present day treatments of a commercial nature which are prescribed and used for the treatment of proliferative skin diseases include three approaches: (1) topical applications: coal tar derivatives, 5 fluorouracil, vitamin A acid, glucocorticoids in high dosage (constituting a non-permissive concentration), bath oils and non-specific emollient creams and ointments; (2) the systemic administration: glucocorticoids and classic anti-cancer agents, for example, emthothrexate, hydroxyurea, azaribine, cyclophosphamide; (3) physical modalities: ultra violet light, x-irradiation, and in severe cases, surgery.

While these treatments provide, in certain cases, some remission of the original symptoms, each treatment suffers some defect, for example, temporary and incomplete mitigation of symptoms, rapid re-occurrence of the disease when mitigation is terminated, serious and sometimes irreversible damage (atrophy) resulting from the topical application for extended times of glucocorticoids, acute bone marrow suppression and cirrhosis of the liver resulting from the protracted use of methothrexate which may lead to death of the patient, and the causation of cancer by the application of anti-cancer drugs, x-irradiation, or ultra violet rays.

In accordance with this invention it has been found that proliferative skin diseases are alleviated, that is, the symptoms of the disease are noticeably improved or become undetectable, by the treatment of the afflicted patient, or animal, with one or more of the pharmaceutical compositions described in detail hereinbelow.

For the purposes of this specification and the claims, a proliferative skin disease is alleviated when there is a noticeable decrease in the thickness of a lesion to palpation, with or without residual redness, or residual slightly dilated blood vessels or residual hyper- or hypopigmentation. For purposes of this invention and the claims hereof, psoriasis is alleviated when a scale-free psoriasis lesion is noticeably decreased in thickness, or noticeably but incompletely cleared or completely cleared.

The compositions may be applied topically or by injection such that the composition enters the blood stream, or intradermally, intra- or peri-lesionally, or sub-cutaneously.

The term "topical" as employed herein relates to the use of the active ingredient incorporated in a suitable pharmaceutical carrier, and applied at the site of the disease for exertion of local action. Accordingly, such topical compositions include those pharmaceutical forms in which the compound is applied externally by direct contact with the skin surface to be treated. Conventional pharmaceutical forms for this purpose include ointments, lotions, pastes, jellies, sprays, aerosols, bath oils and the like. The term "ointment" embraces formulations (including creams) having oleaginous, absorption, water-soluble and emulsion-type bases, e.g., petrolatum, lanolin, polyethylene glycols, as well as mixtures thereof. It has been found that topical application with occlusion of an area larger than the medicated area produces improved results relative to non-occluded topical application and is, therefore, the preferred method of topical treatment with the compositions of this invention.

Certain of the compositions of this invention advantageously include skin penetrating adjuvants such as, for example, dimethyl sulfoxide, dimethyl acetamide, etc.

Injection "intradermally" refers to positioning the composition in the high dermis by needle injection, or by high pressure air injection.

Injection "intra- or peri-lesionally" refers to positioning the composition into the lesion or into the tissue adjacent to the lesion.

The compositions may be injected so as to reach the blood stream intramuscularly, sub-cutaneously, rectally by suppositiories, sublingually, intravenously, orally, by inhalation, or by application to non-diseased skin.

The best mode of practicing the process of this invention is to treat the afflicted animal, or human, so as to cause a continuing release of the active compound at the afflicted site or sites, at a selected, controlled rate which is sustained for an extended time period. For example, epinephrine will be continuously released and provides sustained epinephrine activity for 9–10 hours by employing an aqueous suspension of crystalline epinephrine 1:200, in a sterile solution containing 0.5% phenol, 0.5% sodium thioglycollate, 1% sodium ascorbate, and 25% glycerine in water. This suspension may be administered subcutaneously in a dosage of 0.1–0.3 cc. of the suspension. Epinephrine activity is obtained substantially immediately from the epinephrine in suspension. Various modifications of the suspension ingredients, compatible with the particular active compound selected for injection may be made to obtain the desirable continuing and sustained active compound activity at the site being treated. Moreover, appropriate substitutions for the above mentioned suspension ingredients may be made to accommodate the selected active compound for topical or systemic administration to the afflicted patient, and similar enhanced results are obtained from such applications when the active compound is released over an extended time period.

The compositions of this invention comprise a pharmaceutical carrier and about 0.1% to about 15%, weight/volume, of at least one of the compounds selected from the groups:

I A Compound of the formula

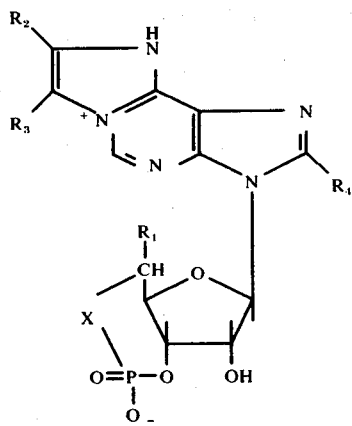

wherein $R_1$ is H or methyl; $R_2$ is H or phenyl; $R_3$ is propyl, isopropyl or phenyl; $R_4$ is H, bromine, methylthio, or benzylthio; X is oxygen or methylene;

II A compound of the formula

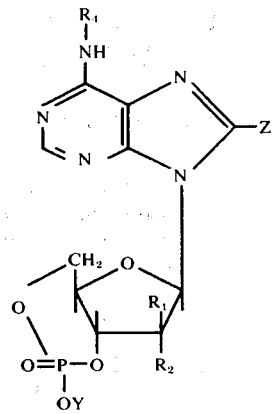

wherein $R_1$ and $R_2$ are hydrogen or hydroxyl; Y is hydrogen or alkali metal; Z is hydrogen, benzylthio, thiol, halogen, alkylthio wherein alkyl is from 1 to 8 carbon atoms, inclusive, and hydroxy; $R_4$ is hydrogen,

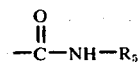

wherein $R_5$ is phenyl, benzyl or alkyl of 1 to 8 carbon atoms;

III A compound of the formula

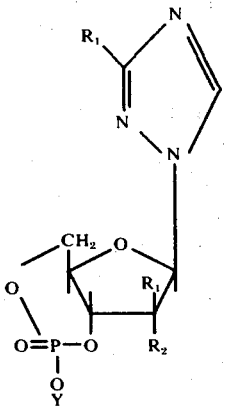

wherein $R_1$ is $-CONH_2$, $-CSNH_2$, $-C(NH)NH_2$, $-C(NH)NHOH$, $-CN$, or $-COOCH_3$; $R_1$ and $R_2$ are hydrogen or hydroxy; Y is hydrogen or alkali metal, said compounds being in association with a pharmaceutical carrier wherein the concentration of said active component is effective to alleviate a proliferative skin disease.

The compositions of this invention may be employed in conjunction with glucocorticoids. The expression "glucocorticoids" refers to a naturally occurring product of the adrenal cortex, or a synthetic analog thereof possessing anti-inflammatory activity and minimal or no mineralocorticoid activity or sex steroid activity. Of the natural glucocorticoids, one may use for example, hydrocortisone or the synthetic glucocorticoids such as methyl prednisolone acetate (Prednisone) for oral application or triamcinolone for topical therapy. The glucocortcoids should be employed in minor amounts or "permissive dosage". The expression "permissive dosage" for glucocorticoids refers to a quantity which minimally supplements the natural output of adrenal cortical glucocorticoids in a normal person and which dosage administered, alone, has no perceptible effect on proliferative skin diseases.

The quantity of the active compound to be used in the compositions of this invention for administration topically, parenterally or systemically ranges from about 0.1% to about 15% weight/volume topically; from about 0.1% to about 10% w/v parenterally; and for oral dosage forms the % amount of active ingredient is determined by the physical characteristics of the carrier with regard to manufacturing requirements and elegance.

The compositions of the present invention are presented for systemic administration to humans and animals in unit dosage forms, such as tablets, capsules, pills, powders, granules, sterile parenteral solutions or suspensions, and oral solutions or suspensions, and oil-water emulsions containing suitable quantities of one or more of the active compounds above described.

For oral administration either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or otherwise compounded to provide a dosage form affording the advantage of prolonged or delayed action or predetermined successive action of the enclosed medication. For example, the tablet can comprise an inner dosage and an outer dosage component, the latter being in the form of an envelope over the former.

Alternatively, the two component system can be utilized for preparing tablets containing two or more incompatible active ingredients. Wafers are prepared in the same manner as tablets, differing only in shape and the inclusion of sucrose or other sweetener and flavor. In their simplest embodiment, capsules, like tablets, are prepared by mixing the active compound or compounds with an inert pharmaceutical diluent and filling the mixture into a hard gelatin capsule or appropriate size. In another embodiment, capsules are prepared by filling hard gelatin capsules with polymeric acid coated beads containing the active compound or compounds. Soft gelatin capsules are prepared by machine encapsulation of a slurry of the active compound or compounds with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared of the insoluble forms with a syrup vehicle with the aid of a suspending agent such as acacia, tragacanth, methylcellulose and the like.

Topical ointments can be prepared by dispersing the active compound or compounds in a suitable ointment base such as petrolatum, lanolin, polyethylene glycol, mixtures thereof, and the like. Advantageously, the active compound or compounds is finely divided by means of a colloid mill utilizing light liquid petrolatum as a levigating agent prior to dispersing in the ointment base. Topical creams and lotions are prepared by dispersing the active compound or compounds in the oil phase prior to the emulsification of the oil phase in water.

For parenteral administration the dosage forms are prepared utilizing the active compound or compounds and a sterile vehicle, water being preferred. The compound, depending on the form and concentration used, can be either suspended or dissolved in the vehicle. In preparing solutions, a water-soluble form of the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution.

For parenteral or systemic administration of the compositions of this invention, the usual dosage of the selected active compound, or compounds, should be employed.

The compositions of this invention may include one or more of the above identified active compounds in a single composition or the method of the invention may be practiced by the administration of a plurality of compositions, each of which contains a single or a plurality of active compounds. In certain cases, the method of the invention may involve the administration of compositions containing a single active compound or a mixture of active compounds by a plurality of the forms of the administration, for example by a combination of oral and/or injection and/or topical application, etc.

In other cases the method of this invention is advantageously practiced by combining the administration forms in a time spaced sequence, for example, by using systemic application of one or more of the compositions for a time period and then applying one or more compositions topically, or by injection while continuing the systemic application, etc.

The following examples identify certain compositions which typify the manner of combining selected active compounds with a pharmaceutical carrier for use in the process of treatment of proliferative skin diseases as above generally described, but they are not intended to represent the limits of either the compositions of or the process of this invention which is defined in the claims.

EXAMPLE 1 — Capsules

One thousand two-piece hard gelatin capsules for oral use, each containing 200 mg. of 8-methylthio-3,5-cyclic-adenosine monophosphate (hereinafter 8-methylthio cAMP) are prepared from the following types and amounts of materials:

| | |
|---|---|
| 8-methylthio cAMP | 200 gm. |
| Corn starch | 150 gm. |
| Talc | 75 gm. |
| Magnesium stearate | 2.5 gm. |

The materials are thoroughly mixed and then encapsulated in the usual manner.

The foregoing capsules are useful for the systemic treatment of psoriasis in adult humans by the oral administration of 1 capsule every 4 hours.

Using the procedure above, capsules are similarly prepared containing in 5, 100, and 500 mg. amounts by substituting 5, 100, and 500 gm. of 8-methylthio cAMP for the 200 gm. used above.

EXAMPLE 2 — Capsules

One thousand two-piece hard gelatin capsules for oral use, each containing 200 mg. of 8-methylthio cAMP are prepared from the following types and amounts of ingredients:

| | |
|---|---|
| 8-methylthio cAMP | 200 gm. |
| Corn starch | 250 gm. |
| Talc | 75 gm. |
| Magnesium stearate | 2.5 gm. |

The ingredients are thoroughly mixed and then encapsulated in the usual manner.

The foregoing capsules are useful for the systemic treatment of psoriasis in adult humans by the oral administration of 1 capsule twice a day.

EXAMPLE 3 — Tablets

One thousand tablets for oral use, each containing 500 mg. of 8-methylthio cAMP are prepared from the following types and amounts of materials:

| | |
|---|---|
| 8-methylthio cAMP | 500 gm. |
| Lactose | 125 gm. |
| Corn starch | 65 gm. |
| Magnesium stearate | 7.5 gm. |
| Light liquid petrolatum | 3 gm. |

The ingredients are thoroughly mixed and slugged. The slugs are broken down by forcing through a number sixteen screen. The resulting granules are then compressed into tablets, each tablet containing 500 mg. of 8-methylthio cAMP.

The foregoing tablets are useful for systemic treatment of psoriasis in adult humans by oral administration of 1 tablet every 4 hours.

EXAMPLE 4 — Oral syrup

One thousand cc. of an aqueous suspension for oral use, containing in each 5 cc. dose 200 mg. of 8-methylthio cAMP is prepared from the following types and amounts of ingredients:

| | |
|---|---|
| 8-methylthio cAMP | 40 gm. |
| Citric acid | 2 gm. |
| Benzoic acid | 1 gm. |
| Sucrose | 700 gm. |
| Tragacanth | 5 gm. |
| Lemon oil | 2 cc. |

-continued

| | |
|---|---|
| Deionized water q.s. | 1000 cc. |

The citric acid, benzoic acid, sucrose, tragacanth, and lemon oil are dispersed in sufficient water to make 850 cc. of solution. The 8-methylthio cAMP is stirred into the syrup until uniformly distributed. Sufficient water is added to make 1000 cc.

The composition so prepared is useful in the systemic treatment of psoriasis in adult humans at a dose of 1 teaspoonful 4 times a day.

EXAMPLE 5 — Parenteral solution

A sterile aqueous solution for intramuscular use, containing in 1 cc. 75 mg. of 8-methylthio cAMP is prepared from the following types and amounts of materials:

| | |
|---|---|
| 8-methylthio cAMP | 75 gm. |
| Lidocaine hydrochloride | 4 gm. |
| Methylparaben | 2.5 gm. |
| Propylparaben | 0.17 gm. |
| Water for injection q.s. | 1000 cc. |

The ingredients are dissolved in the water and the solution sterilized by filtration. The sterile solution is filled into vials and the vials sealed.

The composition is useful in the systemic treatment of psoriasis at a dose of 1 cc. I.M. 4 times a day.

EXAMPLE 6 — Parenteral solution

A sterile aqueous solution for intradermal use, containing in 1 cc. 5 mg. of 8-methylthio cAMP is prepared from the following types and amounts of ingredients:

| | |
|---|---|
| 8-methylthio cAMP | 5 gm. |
| Sodium chloride 10% Solution q.s. | |
| Water for injection q.s. | 1000 cc. |

The 8-methylthio cAMP is added to the water and sufficient sodium chloride added to form an isotonic solution and the solution sterilized by filtration.

The sterile solution is administered intredermally by high pressure injection for treatment of psoriasis.

EXAMPLE 7 — Topical ointment

One thousand gm. of 0.25% ointment is prepared from the following types and amounts of ingredients:

| | |
|---|---|
| 8-methylthio cAMP | 2.5 gm. |
| Liquid petrolatum (heavy) | 250 gm. |
| Wool fat | 200 gm. |
| White petrolatum q.s. | 1000 gm. |

The white petrolatum and wool fat are melted and 100 gm. of liquid petrolatum added thereto. The 8-methylthio cAMP is added to the remaining liquid petrolatum and the mixture milled until the powder is finely divided and uniformly dispersed. The powder mixture is stirred into the white petrolatum mixture and stirring continued until the ointment congeals.

The foregoing ointment is usefully applied topically to the skin of animals for the treatment of mange.

EXAMPLE 8 — Cream

One thousand grams of a topical cream are prepared from the following types and amounts of ingredients:

| | |
|---|---|
| 8-methylthio cAMP | 50 gm. |
| Tegacid Regular* | 150 gm. |
| Spermaceti | 100 gm. |
| Propylene glycol | 50 gm. |
| Polysorbate 80 | 5 gm. |
| Methylparaben | 1 gm. |
| Deionized water q.s. | 1000 gm. |

*Self-emulsifying glyceryl monostearate from Goldschmidt Chemical Corporation, New York, N.Y.

The Tegacid and spermaceti are melted together at a temperature of 70°–80° C. The methylparaben is dissolved in about 500 gm. of water and the propylene glycol, polysorbate 80, and 8-methylthio cAMP are added in turn, maintaining a temperature of 75°–80° C. The methylparaben mixture is added slowly to the Tegacid and spermaceti melt, with constant stirring. The addition is continued for at least 30 minutes with continued stirring until the temperature has dropped to 40°–45° C. The pH of the final cream is adjusted to 3.5 by adding 2.5 gm. of citric acid and 0.2 gm. of dibasic sodium phosphate dissolved in about 50 gm. of water. Finally, sufficient water is added to bring the final weight to 1000 gm. and the preparation stirred to maintain homogeneity until cooled and congealed.

The foregoing composition is useful for the treatment of psoriasis by applying to the lesions with occlusive bandage.

EXAMPLE 9 — Cream

| | |
|---|---|
| 8-methylthio cAMP | 1000 gm. |
| Cetyl alcohol | 600 gm. |
| Stearyl alcohol | 600 gm. |
| Aerosol OT | 150 gm. |
| White petrolatum | 3000 gm. |
| Propylene Glycol | 1000 ml. |
| Distilled Water q.s. | 10000 gm. |

The 8-methylthio cAMP is mixed with the white petrolatum and stirred into a melt of the alcohols and propylene glycol. The aerosol OT is dissolved in 5000 cc. of water and an emulsion formed with the petrolatum mix, sufficient water being added to make 10,000 grams.

The cream is applied to psoriatic lesions twice daily with occlusive bandage.

Optionally following the procedure of the preceding Example substituting 2,000 grams of dimethylacetamide from 2000 grams of water a composition is obtained providing better penetration of the active ingredient into the skin.

EXAMPLE 10

Following the procedure of the preceding Examples 1 to 8, inclusive, substituting a therapeutic dosage amount each of phenyletheno cAMP and methyl-1-(2,3,5-tri-O-benzoyl-β-O-ribofuranosyl) 1,2,4-triazolo-3-3-carboxylate for the 8-methylthio cAMP, compositions are prepared which are useful for the treatment of psoriasis.

EXAMPLE 11

The compositions prepared in the preceding examples 1 through 10, inclusive, can similarly be administered for treatment of atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun induced keratosis, non-malignant keratosis, acne, and seborrheic dermatitis in humans and atopic dermatitis and mange in domesticated animals.

EXAMPLE 12

Advantageously following the therapy of Examples 1 to 10, inclusive, additional benefits can be obtained with concurrent or sequential oral administration of 20 mg. of prednisone twice a week.

I claim:
1. A process for treating proliferating skin diseases which comprises administering to the afflicted human or animal, a composition containing as an active component at least one of the compounds selected from the groups:

I. A compound of the formula

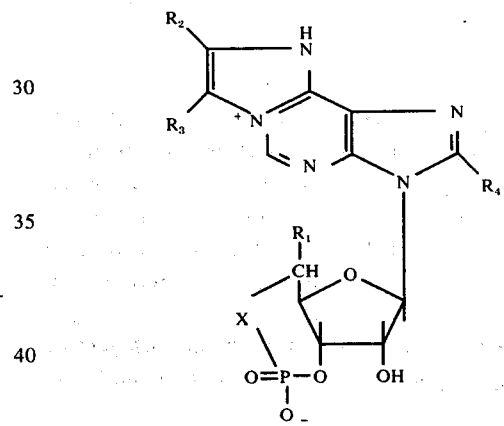

wherein $R_1$ is H or methyl; $R_2$ is H or phenyl; $R_3$ is propyl, isopropyl or phenyl; $R_4$ is H, bromine, methylthio, or benzylthio; X is oxygen or methylene;

II. A compound of the formula

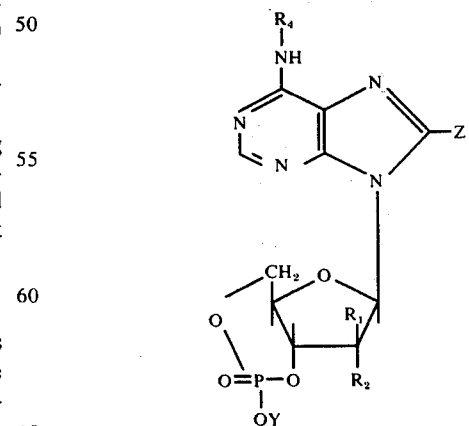

wherein $R_1$ and $R_2$ are hydrogen or hydroxyl; Y is hydrogen or alkali metal; Z is hydrogen, benzylthio, thiol, halogen, alkylthio wherein alkyl is from 1 to 8 carbon atoms, inclusive, and hydroxy; $R_4$ is hydrogen,

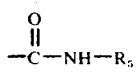

wherein $R_5$ is phenyl, benzyl or alkyl of 1 to 8 carbon atoms;

III. A compound of the formula

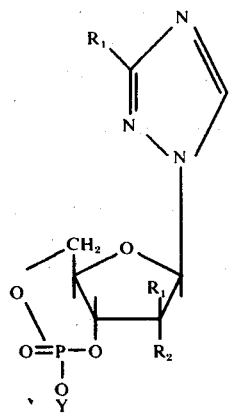

wherein $R_1$ is —CONH$_2$, —CSNH$_2$, —C(NH)NH$_2$, —C(NH)NHOH, —CN, or —COOCH$_3$; $R_1$ and $R_2$ are hydrogen or hydroxy; Y is hydrogen or alkali metal, said compounds being in association with a pharmaceutical carrier wherein the concentration of said active component is effective to alleviate a proliferative skin disease.

2. A process in accordance with claim 1 wherein the said active compound is at least one compound having the formula

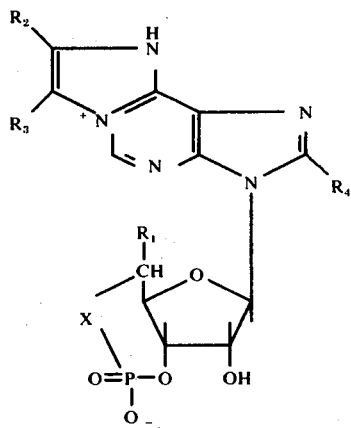

wherein $R_1$ is H or methyl; $R_2$ is H or phenyl; $R_3$ is propyl, isopropyl or phenyl; $R_4$ is H, bromine, methylthio, or benzylthio; X is oxygen or methylene.

3. A process in accordance with claim 1 wherein the said active compound is at least one compound having the formula

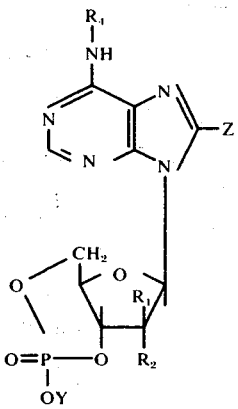

wherein $R_1$ and $R_2$ are hydrogen or hydroxyl; Y is hydrogen or alkali metal; Z is hydrogen, benzylthio, thiol, halogen, alkylthio wherein alkyl is from 1 to 8 carbon atoms, inclusive, and hydroxy; $R_4$ is hydrogen,

wherein $R_5$ is phenyl, benzyl or alkyl of 1 to 8 carbon atoms.

4. A process in accordance with claim 1 wherein the said active compound is at least one compound having the formula

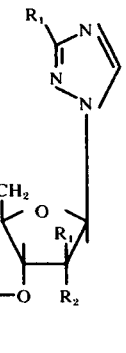

wherein $R_1$ is —COHN$_2$, —CSNH$_2$, —C(NH)NH$_2$, —C(NH)NHOH, —CN, or —COOCH$_3$; $R_1$ and $R_2$ are hydrogen or hydroxy; Y is hydrogen or alkali metal, said compounds being in association with a pharmaceutical carrier wherein the concentration of said active component is effective to alleviate a proliferative skin disease.

* * * * *